(12) United States Patent
Aulbach

(10) Patent No.: US 8,185,904 B2
(45) Date of Patent: May 22, 2012

(54) IMAGE RECONSTRUCTION SYSTEM WITH MULTIPLE PARALLEL RECONSTRUCTION PIPELINES

(75) Inventor: Peter Aulbach, Forchheim-Kersbach (DE)

(73) Assignee: Siemens Aktiengesellschaft, Munich (DE)

( * ) Notice: Subject to any disclaimer, the term of this patent is extended or adjusted under 35 U.S.C. 154(b) by 922 days.

(21) Appl. No.: 12/201,263

(22) Filed: Aug. 29, 2008

(65) Prior Publication Data

US 2009/0064154 A1 Mar. 5, 2009

(30) Foreign Application Priority Data

Aug. 31, 2007 (DE) .................... 10 2007 041 345

(51) Int. Cl.
*G06F 9/46* (2006.01)
*G06F 19/00* (2011.01)
(52) U.S. Cl. ...................................... 718/103
(58) Field of Classification Search .................. None
See application file for complete search history.

(56) References Cited

U.S. PATENT DOCUMENTS

| | | | | |
|---|---|---|---|---|
| 4,737,921 A * | 4/1988 | Goldwasser et al. | ......... | 345/421 |
| 7,728,868 B2 * | 6/2010 | Razzaque et al. | ............... | 348/77 |
| 7,996,839 B2 * | 8/2011 | Farkas et al. | .................. | 718/102 |
| 2004/0119997 A1 * | 6/2004 | Christiansen | ................. | 358/1.13 |
| 2004/0128100 A1 * | 7/2004 | Rotem | ........................... | 702/136 |
| 2004/0196493 A1 | 10/2004 | Christiansen et al. | | |
| 2005/0196030 A1 * | 9/2005 | Schofield et al. | ............. | 382/132 |
| 2006/0095913 A1 * | 5/2006 | Bodas et al. | .................. | 718/100 |
| 2006/0123251 A1 * | 6/2006 | Nakajima et al. | ............. | 713/300 |
| 2006/0146864 A1 * | 7/2006 | Rosenbluth et al. | .......... | 370/458 |
| 2006/0212689 A1 * | 9/2006 | Chaudhry et al. | ............ | 712/228 |
| 2006/0288243 A1 * | 12/2006 | Kim | .............................. | 713/300 |

OTHER PUBLICATIONS

Wijeratne et al, A 96GHZ 65 nm Intel Pentium 4 Processor Execution Core, 2006 IEEE, IEEE Intl. Solid State Circuits conf., 13 pages.*
Sprunt, Brinkley, Pentium 4 Performance Monitoring Features, 2002, IEEE, pp. 72-82.*
"Fixed-Priority Preemptive Multiprocessor Scheduling: To Partition or Not to Partition," Andersson et al., Proc. 7th Int. Conf. on Real-Time Computing Systems and Applications (2000) pp. 337-346.

* cited by examiner

Primary Examiner — Eric Coleman
(74) Attorney, Agent, or Firm — Schiff Hardin LLP

(57) ABSTRACT

In a method, system, computer-readable medium and watchdog module to control a number of medical technology processes that are executed in multiple computerized pipelines according to a predetermined organizational structure, a priority is associated with an incoming process, with a high priority and multiple low priorities being provided. A process with a high priority is executed in a priority pipeline among the multiple pipelines.

13 Claims, 2 Drawing Sheets

IMAGE RECONSTRUCTION SYSTEM WITH MULTIPLE PARALLEL RECONSTRUCTION PIPELINES

BACKGROUND OF THE INVENTION

1. Field of the Invention

The present invention is in the field of process control of multiple, simultaneously occurring processes in a computer system. The present invention has particular utility in the field of reconstruction of medical images in medical data processing systems.

2. Description of the Prior Art

The data quantities that are required for medical images and the associated data, in particular from computed tomography (CT) or positron emission tomography (PET) images, have increased continuously with technological improvements. The images are thereby increasingly more precise, higher-resolution and detailed, which enables a better analysis of the images and a more exact diagnosis; but ever more computing power is required for the reconstruction of the image data into two-dimensional or three-dimensional images. For the clinical daily routine it is very important for the reconstructed images to be available as quickly as possible for further processing or diagnosis and to avoid unnecessary wait times.

In order to meet these requirements, conventional technological efforts have been aimed toward reconstructing the image data into the required images with as much computing power as possible. The reconstruction ensues serially, meaning the reconstruction processes are serially executed one after the other depending on the requirement of images to be reconstructed. One reconstruction process (reconstruction job or task) thus must be terminated first before the next reconstruction process can begin.

This is particularly problematical when multiple reconstruction processes are to be implemented on the same computer, which can be the case when the computer is used both for immediate viewing upon the acquisition of the images (scan) and in the treatment and diagnosis at a later point in time. The same computer also is often used remotely from other workstations for reconstruction of image data.

The use of one computer is also problematic when the computer should likewise implement reconstructions of acquired images of a CT or PET system in real time, thus during the scanning of the images. It is important (in particular during the examination of a patient, thus during the scanning) that these images can be observed and analyzed immediately in order to be able to make corrections if necessary during the scan process or in order to be able to use first findings from the images just acquired for further implementation of the medical procedure.

If a reconstruction process for other images (for example remotely from another workstation) is already being processed on the computer in an imaging processing procedure or analysis procedure, this computer must first finish the already running reconstruction process before it can begin with the reconstruction process for the real time scan procedure.

Burdensome and time-wasting wait times therefore arise for the user, particularly for the medical professionals who conduct the examinations on patients. These wait times become longer as more reconstruction processes are present in the wait list (queue) or wait loop of the computer and that are executed before the scan reconstruction process is begun.

SUMMARY OF THE INVENTION

An object of the present invention is to provide a method, a computer program product, a watchdog module and a system with which medical data (in particular 2-dimensional and 3-dimensional medical images) can be reconstructed quickly and efficiently.

The present invention is based on associating operating system components or sub-systems and/or resources for processes (in particular processing medical images) in the context of a method and system for implementing a number of computerized processes, wherein the computer has a number of pipelines, and wherein a high priority or at least one low priority is respectively associated with a process. In the method and system according to the invention, for each process among the multiple processes that is requested, a determination of the priority is associated with the requested process is made, the requested process is assigned to at least one predetermined priority pipeline from multiple pipelines in the event that a high priority is associated with the requested process and otherwise the requested process is assigned to one of the pipelines when or as soon as a pipeline is available, and the availability of the priority pipeline is perpetually monitored.

The processes can be medical technology processes such as the reconstruction of a medical image (known as reconstruction jobs) that generate two-dimensional or three-dimensional images from medical data of a computed tomography (CT) apparatus and/or a positron emission tomography (PET) apparatus or other imaging apparatuses in order to output such images on a display device. The data can be stored in a database or can be made directly available by the scanning apparatus (which can be similar to a CT and/or PET system or the like known in the prior art).

Processes can be requested by the CT or PET system that is implementing the ongoing scan procedure and that should display the corresponding images. Processes can also be requested by other workstations that display the images for processing, diagnosis, analysis or for additional treatments. The workstations can be arranged at other locations, for example distributed throughout a clinic or various physicians' practices, and the processes can be requested "remotely" at the computer via a remote access.

According to the invention, a priority is associated with each job or each process, so different or identical priorities can be associated with various processes. A number of priority levels can be provided for this purpose, but it is required that at least one level of high priority and at least one level with lower priority are provided.

A higher priority than others can thus be associated with specific processes. For example, the higher or high priority can be associated with an ongoing scan process of a medical apparatus. This means that the high priority is associated with the data that are transmitted from the scanning apparatus and should be made available to the medical personnel as quickly as possible. According to the invention, the priority pipeline is thus assigned to such scan process data, so the execution of the process ensues promptly with high priority.

The assignment of a process to a pipeline can involve determining which process is to be executed in which pipeline, with the determination being made on the basis of physical location or chronologically. The assignment can also include the automatic implementation or execution of the process in the corresponding pipeline.

The pipelines can execute the respective processes assigned to them in parallel with one another.

A separate processor and/or processor core of the computer can be respectively associated with each pipeline. This means that each pipeline constitutes a processor that can independently reconstruct a corresponding image from a data set.

Each pipeline (process channel) is therefore available and usable independently of the other pipelines.

Alternatively, a pipeline can be defined as a data stream, and the computing power available in a system can be divided into various pipelines, for example at the operating system or software level.

The number of the pipelines depends on the available system and (as long as it is at least two) is not limited in the context of the invention.

The method according to the invention is implemented for each process to be handled or requested. This means that, upon occurrence or receipt of a request to implement a process, its priority is respectively determined and the appropriate pipeline can then be associated with the process. It is possible to implement the method upon the occurrence of a process, for example when the command to execute a process arrives at the computer. A wait list or wait loop for processes to be executed can also be generated that is interrogated at intervals in order to implement the method according to the invention.

Through the assignment of a process with high priority to the priority pipeline it is ensured that such processes with high priority can always be executed quickly. The priority pipeline therefore can be reserved for processes with high priority and used only to execute such processes. Processes with high priority can be the aforementioned scan processes. It is possible for only one scan device (CT/PET) to be associated with the system, so that only one scan process can occur at a time. Alternatively, the system can encompass multiple imaging modalities.

Alternatively or cumulatively, the priority pipeline can be cleared for a process with high priority as soon as the process with high priority (for example the scan process) is prepared or started. For example, the priority pipeline can then be cleared when a scan (thus the acquisition of images) is started or prepared with the medical apparatus, since then it is to be expected that the data to be reconstructed for an image will be transmitted within a short period of time. If an additional process with lower priority is already being executed in the priority pipeline, this process can be interrupted and continued again when the process with high priority has been ended. The interrupted process could also be shifted to one of the other pipelines with lower priority.

The perpetual monitoring of the availability of the pipelines enables a fast and efficient redistribution of the processes to be executed. The perpetual monitoring can ensue periodically or continuously.

The perpetual monitoring of the availability ensures an optimal utilization of the existing computing capacity.

In addition to the availability of the pipelines, the performance of at least the priority pipeline, but also of the other pipelines, in the execution of the respective assigned processes can additionally be monitored. Given unsatisfactory performance of a pipeline, for example if the process assigned to it requires more computing power than the pipeline can provide, portions of this process can be transferred into other pipelines if these are free and available.

The monitoring of the availability and performance can ensue at the processor level by the current capacity of the processor being perpetually monitored.

A watchdog module, which is connected with each of the pipelines and monitors their state, can be provided to monitor the availability and performance. The watchdog module can additionally access the individual pipelines and monitor and control the processes running in these pipelines.

For this purpose, a threshold can be predetermined in order to quantify the performance so that the process is divided into sub-processes if the predetermined threshold is not satisfied in the execution of the process in a pipeline. Furthermore, a first of the sub-processes can be executed in the pipeline while an additional pipeline is provided for the other divided sub-process.

The provision of additional pipelines is particularly advantageous for processes of high priority, in particular for scan processes, but it can also be used for any other low-ranking process.

The process (in particular if a low-ranking priority is associated therewith) can also be relegated to a wait loop if no pipeline is available at the point in time of the assignment. The processes located in the wait loop are then distributed in order in the pipelines as soon as a pipeline is available.

The low priority category can be sub-divided into different priorities. For example, a first low priority and a second low priority can be provided, wherein the first low priority can be classified higher than the second low priority such that a process with which a first low priority is associated is preferentially assigned to a pipeline relative to a process with which the second low priority is associated.

For example, if a wait loop is used, a process with first low priority can be inserted into the wait loop at a first point so that it is assigned to a pipeline as soon as the next pipeline is free.

However, a second priority pipeline can also be provided that is reserved either for processes with which a first low priority is associated, or that (as described above with regard to the priority pipeline) is freed of already-running processes as soon as a process with first low priority occurs.

It is understood that the number of provided priority levels can be arbitrarily expanded and is in no way limited to a maximum of three priority levels described in this example.

The number of the available pipelines can be adapted to the system depending on the requirements and is not limited by the invention to a specific number of pipelines.

The embodiments of the method according to the invention that are described above can also be implemented as a computer-readable medium that causes a computer to implement the method according to the invention that is described above, by means of program code, stored in the medium, executed by a processor.

Moreover, it is possible that individual components to implement the method described above be executed as a commercial unit and the remaining components can be executed in another commercial unit (such as a distributed system). For example, the watchdog module represents such a commercial unit.

DESCRIPTION OF THE PREFERRED EMBODIMENTS

Figure 1:
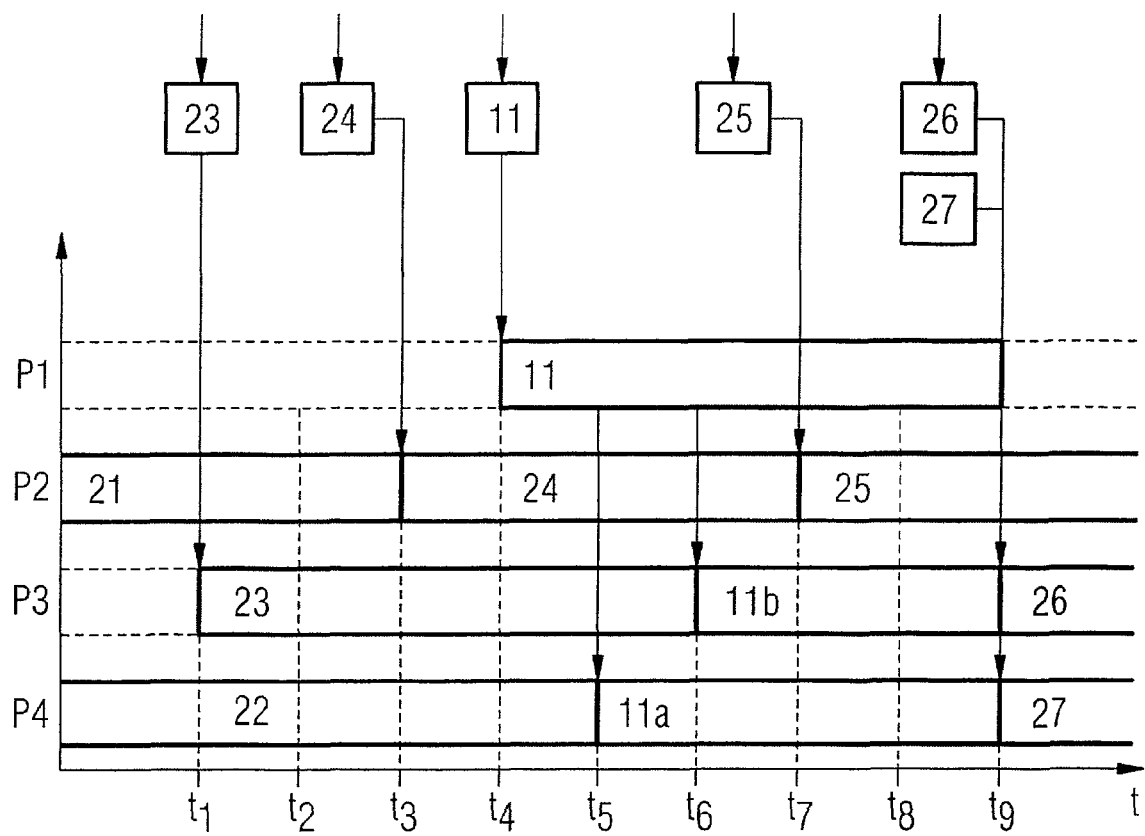
FIG. 1 schematically illustrates the control of the execution of a number of processes in a number of pipelines according to a first embodiment of the invention.

FIG. 1 schematically shows the control of the execution of a number of processes in four pipelines P1, P2, P3 and P4. Each pipeline may be its own processor or processor core that can independently execute processes such as reconstruction processes of 2-dimensional or 3-dimensional images. Up to four processes thus can run simultaneously, in parallel with one another, in the four pipelines. The individual pipelines are independent of one another in the execution of the processes and can respectively independently execute processes.

It is understood that the number of four pipelines is only exemplary, and that any arbitrary number X of pipelines can be used according to the invention.

In the embodiment shown in FIG. 1, the pipeline P1 is reserved for processes of high priority and is cleared for such processes. The pipeline P1 is therefore designated in the following as a priority pipeline. The priority pipeline is preferably reserved for reconstruction jobs of the scan device, for example the CT and/or PET system. A low priority is associated with other processes, for example reconstruction jobs for subsequent local image processing of medical image data or remote jobs from remote workstations. The processes with low priority are then distributed to the other pipelines P2, P3 or P4.

If a command or order to execute a third reconstruction job or process 23 now occurs at a point in time t1, it is initially checked as to which priority is associated with this process 23. In this example, a low priority is associated with the third process 23 since this concerns, for example, the reconstruction of already-stored image data for the purpose of additional processing. Since the first pipeline P1 is in this case reserved as a priority pipeline for processes with high priority, the newly occurring (arriving) third process 23 must be assigned to one of the other pipelines P2, P3 or P4. Since, at the point in time t1, a first process 21 with low priority is already being executed in the pipeline P2 and a second process 22 (likewise with low priority) is already being executed in the pipeline P4, these pipelines are presently in use, and the third process is assigned to the pipeline P3 and the execution starts immediately.

If a command or order to implement an additional, fourth, likewise subordinate process 24 occurs at the point in time t2, neither the pipeline P2 nor the pipelines P3 or P4 can be assigned to this since the first, second and third processes 21, 22 or 23 are still being executed in these pipelines. However, the low-ranking fourth process 24 will be assigned to the pipeline P2 and executed there as soon as the first process 21 in pipeline P2 ends at the point in time t3, for example.

In this embodiment, the priority pipeline P1 thereby remains free so that, if a process with high priority 11 occurs at a point in time t4, this can in every case be immediately assigned to the priority pipeline P1 so that the execution of the process with high priority is started as quickly as possible. No wait times thus arise for processes with high priority, in particular for the reconstruction of images from scan processes, and the processes can be implemented as quickly as possible even given otherwise high utilization of the overall system. The wait times for the users (thus, for example, for the medical personnel) are thus advantageously reduced.

The assignment or work distribution of the individual pipelines is perpetually monitored by a watchdog module. The watchdog module can periodically query the state of the pipelines and thus establish at every point in time whether a process is being executed in the respective pipeline and, if so, which.

The watchdog module can also respectively be informed about the start or, respectively, the end of a process, such that it continuously knows the workflow and the utilization of the pipelines.

The watchdog module can be connected with the pipelines and directly take over the process control.

The watchdog module can be executed as a computer program product or as a hardware component and be integrated into the system for image reconstruction (image reconstruction system; IRS) or can be added as an auxiliary module.

Moreover, the watchdog module can also monitor the performance of the individual pipelines and, if it is established that the process with high priority 11 demands more computing power than can be provided by the priority pipeline P1, can assign a second pipeline to this process, such that this process with high priority 11 is also simultaneously implemented distributed over multiple pipelines. For example, if the watchdog module determines at the point in time t5 that the performance of the process with high priority 11 is insufficient, it swaps out the portion of the process with high priority 11 as a first sub-process 11a to pipeline P4 since the second process 22 in pipeline 24 has ended at this point in time.

In the event that the process with high priority 11 still exhibits insufficient performance, a second sub-process 11b of the process with high priority 11 can be swapped to the pipeline P3 at the point in time t6 at which the third process 23 in pipeline P3 ends. The process with high priority 11 is thus in this case distributed to three pipelines and executed in parallel, which further increases the performance and correspondingly reduces the wait time for the user.

The pipeline P2 can thereby be kept open for low-ranking processes so that a possibly occurring additional, fifth, low-ranking process 25 is assigned to pipeline P2 at the point in time t7 as soon as the fourth low-ranking process 24 in pipeline P2 ends.

If additional, low-priority, sixth and seventh processes 26 and 27 occur at a later point in time t8 while the process with high priority 11 with the and second sub-processes 11a and 11b are still being implemented in pipelines P1, P3 and P4, these cannot be immediately assigned since pipeline P2 still executes the fifth process 25. However, the sixth low-ranking process 26 and the seventh low-ranking process 27 can be associated with the freed pipelines P3 or, respectively, P4 and be executed in these as soon as the process with high priority 11 (and therefore also the swapped-out first and second sub-processes 11a in pipeline P4 and 11b in pipeline P3) is ended. In this embodiment the priority pipeline P1 remains free in no-load operation for processes with which a high priority is associated and waits for a further process with high priority.

It is understood that the points in time and the order are stated only for illustrative purposes, and that arbitrarily many variations for the existence of processes can occur within the invention, and that other forms of the assignment are possible.

A wait loop can also be provided in which, for example, the sixth low-ranking process 26 and the seventh low-ranking process 27 can be arranged at the point in time t8, wherein then the watchdog module extracts the processes in order from the wait loop upon freeing up the pipelines P3 and P4 and assigns these processes to the freed pipelines.

Figure 2:
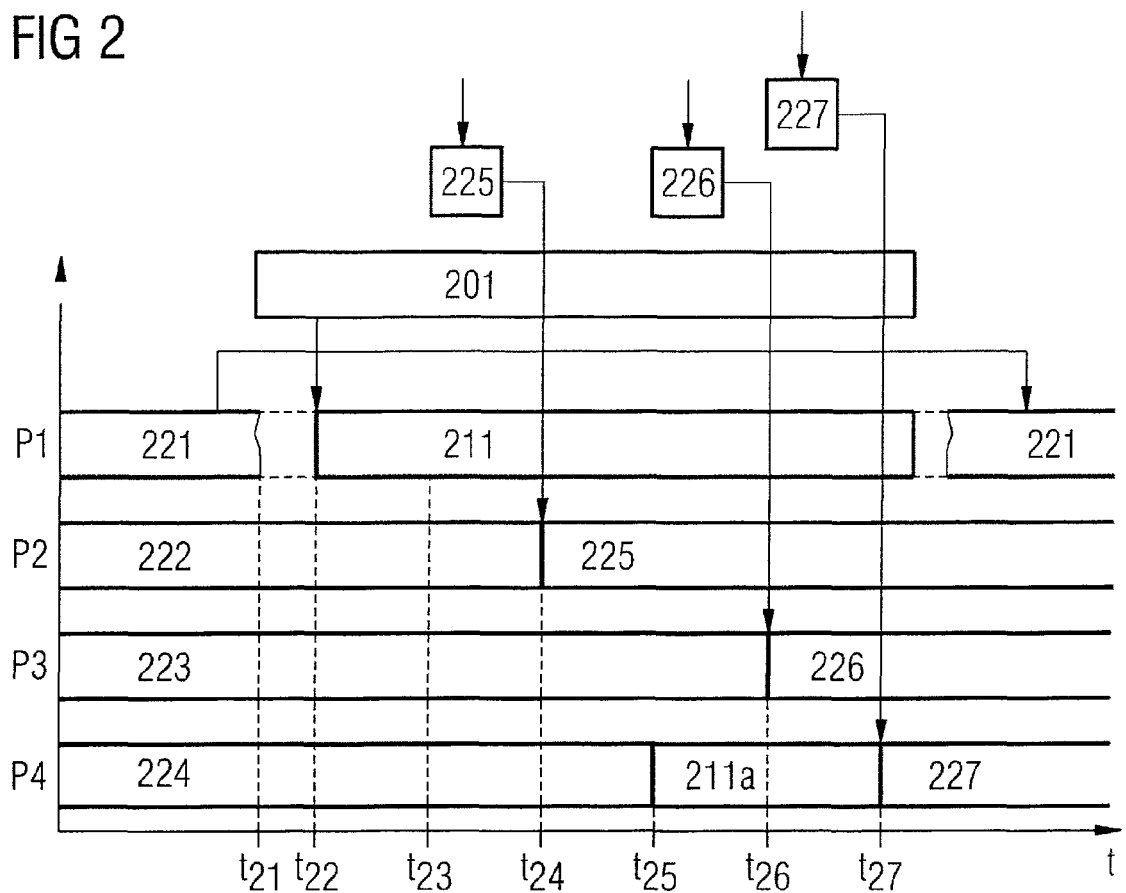
FIG. 2 schematically illustrates the control of the execution of a number of processes in a number of pipelines according to a second embodiment of the invention.

FIG. 2 shows an assignment overview of a number of processes to likewise four pipelines according to a second embodiment of the invention. The distribution of the processes and the pipelines is thereby identical to that described with regard to FIG. 1. The pipeline P1 is also in this case a priority pipeline; however, in contrast to the embodiment described in FIG. 1, low-ranking processes are also executed in the priority pipeline when the priority pipeline P1 is not required for a process with high priority and the other pipelines p2, P3 and P4 are already occupied with other low-ranking processes.

In the example presented here, for example, before the point in time t21 the second low-ranking process 222 is executed in pipeline P2, the third low-ranking process 223 is executed in pipeline P3 and the fourth low-ranking process 224 is executed in pipeline P4. The first low-ranking process 221 is additionally executed in the priority pipeline.

If a scan process 201 is now started at a medical modality (such as, for example, a computed tomography (CT) scanner, a positron emission tomography (PET) scanner or the like) at the point in time t21 such that data for a reconstruction with high priority are expected soon, the first low-ranking process 221 in the priority pipeline P1 is interrupted and the priority pipeline P1 is cleared for the expected process with high priority 211. If the process 211 is then requested at the point in time t22, this can be immediately assigned to the priority pipeline P1 and executed in this.

The other pipelines P2, P3 and P4 remain unaffected by this, and the respective second, third or, respectively, fourth process 222, 223 or, respectively, 224 running in these is further executed. A possible fifth low-ranking process 225 possibly occurring at the point in time t23 can thus be assigned to the next freed pipeline (in this example pipeline P2 at the point in time t24 at which the second process 222 ends). Following this, the fifth low-ranking process 225 is directly assigned to the pipeline P2 and its execution on pipeline P2 is started.

If the watchdog module establishes at a point in time t25 that the performance (for example in the execution of the process with high priority 211) is insufficient and lies below a predetermined threshold, a portion of this process can (as already described with regard to the first embodiment with reference to FIG. 1) be transferred out to another pipeline such as (in this case) pipeline P4, which is free at the point in time t25 since the fourth process 224 is ended then. A portion of the process with high priority 211 can thus be executed as a first sub-process 211a in pipeline P4.

Additionally occurring sixth and seventh low-ranking processes 226 and 227 can then be distributed to the pipelines as soon as one of these pipelines becomes available, which is perpetually monitored by the watchdog module. For example, if the pipeline P3 becomes free at the point in time t26 since the third low-ranking process 223 has ended, the newly arrived sixth low-ranking process 226 can be started therein. If the process with high priority 211 (and with it the transferred first sub-process 211a as well) is ended at the point in time t27, the priority pipeline P1 becomes free insofar as an additional scan process (and therefore an additional process with high priority) is not immediately started afterward. The first low-ranking process 221 (which was already begun before but interrupted) can then be picked up again and ended as long as no additional process with high priority occurs.

In this example, the pipeline P4 also becomes free at the point in time t27, such that the seventh low-ranking process 227 can be assigned thereto and started.

Additional clear possibilities in this embodiment are also apparent to those skilled in the art. For example, it is thus possible to also continue the interrupted first low-ranking process 221 in pipeline P2 at the point in time t24 in order to end this already-started process more quickly. In this case, the fifth low-ranking process 225 would then have to be correspondingly shifted further back and only be executed in pipeline P3 at the point in time t26, since the pipeline P3 only becomes free at this point in time t26. In this case the sixth and seventh low-ranking processes would have to wait somewhat longer for the next freed pipelines.

Figure 3:
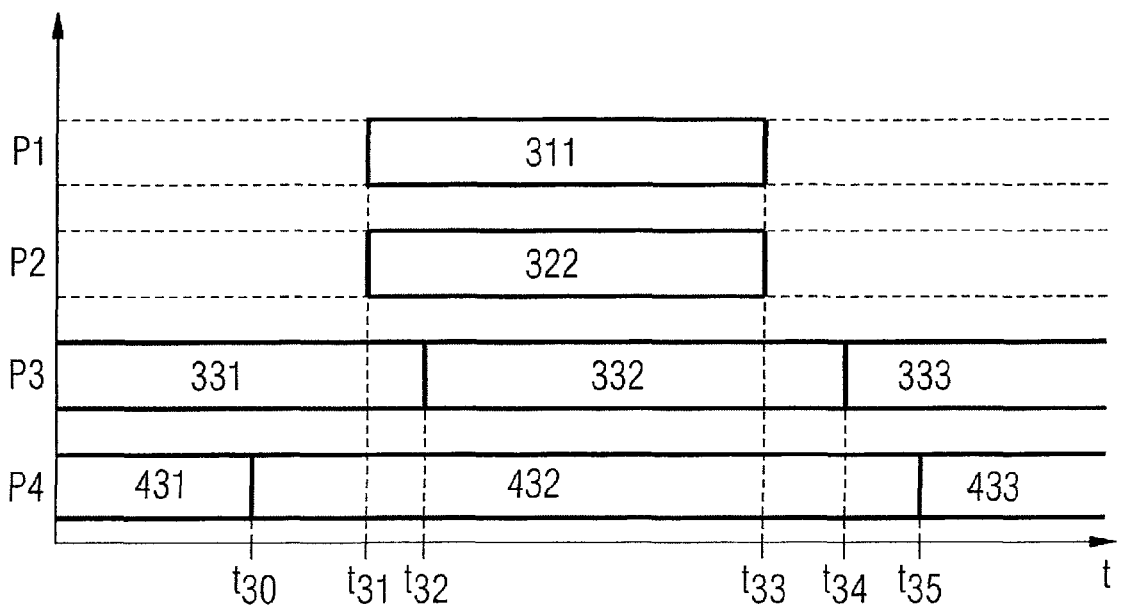
FIG. 3 schematically illustrates the control of the execution of a number of processes in a number of pipelines according to a third embodiment of the invention.

FIG. 3 shows an assignment overview of a number of processes according to a third embodiment in which the pipelines P1, P2, P3 and P4 are respectively reserved for specific process types. The priority pipeline P1 is reserved for processes with high priority, such that the process with high priority 311 can be started immediately at the point in time t31 upon occurrence of such a process (which can again be a scan process).

Moreover, the pipeline P2 can be kept free for a second process with first low priority. This can, for example, be a process 322 with first low priority that can likewise be assigned to pipeline P2 and immediately be executed in this at a point in time t31 or at another arbitrary point in time since the pipeline P2 is specifically reserved for this type of process. Processes of high priority and processes of first low priority can thus be executed simultaneously or offset from one another, quickly and without time delay, at any arbitrary point in time.

The pipeline P3 can then be designated for processes of a second low priority, such that such processes of second low priority (for example a first, a second and a third process 331, 332 or, respectively, 333 of second low priority) can be assigned to the pipeline P3 and be executed in this in the order of their occurrence or in a different order.

The pipeline P4 can then be used for processes of additional low priority classes, for example for a first, second and third process 431, 432 and 433 of third priority which are then executed in order in the pipeline P4.

It is understood that the principles of the embodiments presented in FIGS. 1, 2 and 3 can be mixed, such that (for example) in the case of the embodiment of FIG. 3 the pipelines P1 and P2 are respectively reserved for processes of high priority and first low priority but the pipelines P3 and P4 are freely available for additional processes of low priority, and these additional processes of low priority can be freely distributed to said pipelines P3 and P4 as described with reference to FIG. 1 for the low-ranking processes.

Naturally, it is also possible that the reserved pipelines P1 and/or P2 are not kept free in spite of their priority, but rather likewise can be tasked with low-ranking processes, wherein these are then interrupted as soon as a process with high priority occurs for the priority pipeline P1, or with first low priority for the pipeline P2, such that the low-ranking processes in these pipelines are then interrupted as described with regard to FIG. 2 for the priority pipeline P1.

This specification enables those skilled in the art to devise a number of implementations in order to distribute the various processes (that should be executed as quickly as possible to reconstruct medical images) to various simultaneously operating pipelines. An optimal utilization of the pipelines (and therefore of the resources) is thereby ensured. The wait times for the users in order to wait for the reconstruction of the medical images are thereby optimized.

Those skilled in the art also will recognize that the invention can be realized partially or entirely in software and/or hardware and/or distributed on multiple physical products (in particular also computer program products).

Although further modifications and changes may be suggested by those skilled in the art, it is the intention of the inventor to embody within the patent warranted hereon all changes and modifications as reasonably and properly come within the scope of his contribution to the art.

I claim as my invention:

1. A method for controlling a plurality of computerized processes relating to medical examinations comprising the steps of:
   in a computerized data processing system, providing a plurality of processing pipelines wherein, in each of said pipelines, data associated with respective medical examination procedures are processed independently of processing in other pipelines;

among a plurality of processes to be respectively processed in said pipelines, assigning one of said processes, that represents scanning of an examination subject by a medical imaging modality, a high priority that is higher than respective priorities assigned others of said processes;

upon arrival of each incoming process at said computerized system, determining the priority associated with the incoming process;

if said incoming process has said high priority associated therewith, assigning said incoming process to at least one predetermined priority pipeline, among said plurality of pipelines and processing said incoming process in said priority pipeline by reconstructing an image of the examination subject from said scanning, and otherwise assigning said incoming process for processing in a pipeline, other than said priority pipeline, in said plurality of pipelines, as soon as said pipeline other than said priority pipeline is available;

unless and until a process associated with said high priority arrives at said computerized system as said incoming process, using said priority pipeline to process processes in said plurality of processes other than said process associated with said high priority, and interrupting processing in said priority pipeline if and when a process associated with said high priority arrives at said computerized system as said incoming process; and while said computerized system is operational, perpetually monitoring availability of said priority pipeline.

2. A method as claimed in claim 1 comprising executing said plurality of processes in parallel respectively in said plurality of pipelines.

3. A method as claimed in claim 1 comprising individually associating respective computer processors with the respective pipelines in said plurality of pipelines.

4. A method as claimed in claim 1 comprising maintaining said priority pipeline free for immediate use by an incoming process associated with said high priority.

5. A method as claimed in claim 1 comprising arranging incoming processes among said plurality of processes, other than said process associated with said high priority, in a weight loop when no pipeline in said plurality of pipelines is available at a time of arrival of said processes in said weight loop.

6. A method as claimed in claim 1 comprising providing further priorities, other than said high priority, comprising at least a first low priority and a second low priority, each having a lower priority than said high priority.

7. A method as claimed in claim 6 comprising preferentially assigning an incoming process associated with said first low priority to a pipeline among said plurality of pipelines for processing, relative to an incoming process having said second low priority associated therewith.

8. A method as claimed in claim 6 comprising designating one of said plurality of pipelines, other than said priority pipeline, as a further priority pipeline, and processing an incoming process having said first low priority associated therewith in said further priority pipeline.

9. A method as claimed in claim 1 comprising monitoring performance of processing in said priority pipeline during processing of said process therein having said high priority.

10. A method as claimed in claim 9 comprising monitoring said performance relative to a predetermined threshold, and transferring processing of said process associated with said high priority from said priority pipeline to a different one of said pipelines in said plurality of pipelines if said performance of said processing in said priority pipeline fails to satisfy said threshold.

11. A computer-readable medium encoded with programming instructions for controlling a plurality of computerized processes relating to medical examinations in a computerized data processing system, having a plurality of processing pipelines wherein, in each of said pipelines, data associated with respective medical examination procedures are processed independently of processing in other pipelines, said programming instructions causing said computerized system to:

among a plurality of processes to be respectively processed in said pipelines, assign one of said processes, that represents scanning of an examination subject by a medical imaging modality, a high priority that is higher than respective priorities assigned others of said processes;

upon arrival of each incoming process at said computerized system, determine the priority associated with the incoming process;

if said incoming process has said high priority associated therewith, assign said incoming process to at least one predetermined priority pipeline, among said plurality of pipelines and processing said incoming process in said priority pipeline by reconstructing an image of the examination subject from said scanning, and otherwise assign said incoming process for processing in a pipeline, other than said priority pipeline, in said plurality of pipelines, as soon as said pipeline other than said priority pipeline is available;

unless and until a process associated with said high priority arrives at said computerized system as said incoming process, use said priority pipeline to process processes in said plurality of processes other than said process associated with said high priority, and interrupt processing in said priority pipeline if and when a process associated with said high priority arrives at said computerized system as said incoming process; and while said computerized system is operational, perpetually monitor availability of said priority pipeline.

12. A watchdog module connected in a computerized data processing system, having a plurality of processing pipelines wherein, in each of said pipelines, data associated with respective medical examination procedures are processed independently of processing in other pipelines, and wherein among a plurality of processes, that represents scanning of an examination subject by a medical imaging modality, to be respectively processed in said pipelines, one of said processes is assigned a high priority that is higher than respective priorities assigned others of said processes, and wherein upon arrival of each incoming process at said computerized system, determining the priority associated with the incoming process is determined, and wherein if said incoming process has said high priority associated therewith, said incoming process is assigned to at least one predetermined priority pipeline by reconstructing an image of the examination subject from said scanning, among said plurality of pipelines and said incoming process is processed in said priority pipeline, and wherein said incoming process is otherwise assigned for processing in a pipeline, other than said priority pipeline, in said plurality of pipelines, as soon as said pipeline other than said priority pipeline is available and wherein unless and until a process associated with said high priority arrives at said computerized system as said incoming process, said priority pipeline is used to process processes in said plurality of processes other than said process associated with said high priority, and wherein processing in said priority pipeline is interrupted if and when a process associated with said high priority arrives at said computerized system as said incoming process, and, said watchdog module being configured to perpetually monitor availability of said priority pipeline while said computerized system is operational.

13. A system for controlling a plurality of computerized processes comprising:

a computerized data processing system comprising a plurality of processing pipelines wherein, in each of said pipelines, data associated with respective medical examination procedures are processed independently of processing in other pipelines, said data processing system being configured to assign, among a plurality of processes to be respectively processed in said pipelines, at toast one of said processes, that represents scanning of an examination subject by a medical imaging modality, a high priority that is higher than respective priorities assigned others of said processes, and to determine, upon arrival of each incoming process at said computerized system, the priority associated with the incoming process, and, if said incoming process has said high priority associated therewith, to assign said incoming process to at least one predetermined priority pipeline, among said plurality of pipelines and to process said incoming process in said priority pipeline by reconstructing an image of the examination subject from said scanning, and to otherwise assign said incoming process for processing in a pipeline, other than said priority pipeline, in said plurality of pipelines, as soon as said pipeline other than said priority pipeline is available, and wherein unless and until a process associated with said high priority arrives at said computerized system as said incoming process, said priority pipeline is used to process processes in said plurality of processes other than said process associated with said high priority, and wherein processing in said priority pipeline is interrupted if and when a process associated with said high priority arrives at said computerized system as said incoming process; and a watchdog module configured to perpetually monitor availability of said priority pipeline while said computerized system is operational.

\* \* \* \* \*